United States Patent
Ertel et al.

(10) Patent No.: US 12,019,041 B2
(45) Date of Patent: Jun. 25, 2024

(54) PORTABLE DIELECTRIC SPECTROSCOPY DEVICE

(71) Applicant: XaTek, Inc., Chagrin Falls, OH (US)

(72) Inventors: Jason R. Ertel, Twinsburg, OH (US); Shawn Dellinger, Cleveland, OH (US); Jason Grant Tilk, Cleveland Hts., OH (US)

(73) Assignee: XATEK, INC., Chagrin Falls, OH (US)

( * ) Notice: Subject to any disclaimer, the term of this patent is extended or adjusted under 35 U.S.C. 154(b) by 512 days.

(21) Appl. No.: 17/295,136

(22) PCT Filed: Nov. 14, 2019

(86) PCT No.: PCT/US2019/061368
§ 371 (c)(1),
(2) Date: May 19, 2021

(87) PCT Pub. No.: WO2020/106536
PCT Pub. Date: May 28, 2020

(65) Prior Publication Data
US 2022/0003703 A1    Jan. 6, 2022

Related U.S. Application Data (60) Provisional application No. 62/769,593, filed on Nov. 20, 2018.

(51) Int. Cl.
*G01N 27/02* (2006.01)
*G01N 33/487* (2006.01)

(52) U.S. Cl.
CPC ..... *G01N 27/026* (2013.01); *G01N 33/48707* (2013.01)

(58) Field of Classification Search
CPC .. G01N 27/026; G01N 33/48707; G01V 3/30; G01V 3/38
See application file for complete search history.

(56) References Cited

U.S. PATENT DOCUMENTS

| | | | |
|---|---|---|---|
| 4,929,426 A * | 5/1990 | Bodai | G01N 33/4925 422/403 |
| 5,515,240 A | 5/1996 | Rodeffer | |

(Continued)

FOREIGN PATENT DOCUMENTS

| | | |
|---|---|---|
| CN | 106102460 A | 11/2016 |
| CN | 107548462 B | 12/2020 |

(Continued)

OTHER PUBLICATIONS

O. Cakmak et al., A cartridge based sensor array platform for multiple coagulation measurements from plasma, Lab Chip, 2015, 15, 113 (Year: 2015).*

(Continued)

*Primary Examiner* — Daniel R Miller
(74) *Attorney, Agent, or Firm* — Rankin, Hill & Clark LLP (57) ABSTRACT

A portable DS device includes a device housing, device-side electrical contacts, a computing system and a removable sensor receiver assembly. The device housing includes a removable sensor receiver compartment. The device-side electrical contacts are positioned in or adjacent to the removable sensor receiver compartment. The computing system is in communication with the device-side electrical contacts and includes an impedance analyzer. The removable sensor receiver assembly includes a removable sensor receiver housing selectively receivable in and removable from the removable sensor receiver compartment. The removable sensor receiver housing includes a fluid sensing apparatus receiving section that receives a fluid sensing apparatus in which a fluid to be tested is loaded. The removable sensor receiver assembly provides for an electrical connection between the associated fluid sensing apparatus and the device-side electrical contact when the remov- (Continued)

able sensor receiver housing is received in the removable sensor receiver compartment.

20 Claims, 7 Drawing Sheets (56) References Cited

U.S. PATENT DOCUMENTS

| | | | |
|---|---|---|---|
| 5,821,399 A * | 10/1998 | Zelin | G01N 27/3271 |
| | | | 73/1.02 |
| 5,871,365 A | 2/1999 | Kajiura | |
| 6,028,433 A | 2/2000 | Cheiky-Zelina | |
| 6,066,243 A * | 5/2000 | Anderson | G16H 40/63 |
| | | | 422/82.01 |
| 6,193,864 B1 * | 2/2001 | Leader | G01N 33/4915 |
| | | | 205/789.5 |
| 6,352,630 B1 | 3/2002 | Frenkel | |
| 6,449,580 B1 | 9/2002 | Bardetsky | |
| 7,005,857 B2 | 2/2006 | Stiene et al. | |
| 7,497,997 B2 | 3/2009 | Glezer et al. | |
| 8,012,745 B2 | 9/2011 | Glezer et al. | |
| 8,450,078 B2 | 5/2013 | Dennis et al. | |
| 8,641,986 B2 | 2/2014 | Glezer et al. | |
| 8,852,922 B2 | 10/2014 | Glezer et al. | |
| 8,961,903 B2 | 2/2015 | Iñaki Sádaba Champetier De Ribes et al. | |
| 9,149,215 B2 | 10/2015 | Werner et al. | |
| 9,213,036 B2 | 12/2015 | Iñaki Sádaba Champetier De Ribes et al. | |
| 9,404,881 B2 | 8/2016 | Glezer et al. | |
| 9,816,956 B2 | 11/2017 | Werner | |
| 9,903,877 B2 | 2/2018 | Zhao et al. | |
| 9,910,053 B2 | 3/2018 | Bakhru | |
| 9,921,232 B2 | 3/2018 | Collier et al. | |
| 2003/0067297 A1 | 4/2003 | Hanisch | |
| 2003/0224523 A1 * | 12/2003 | Thornberg | B01L 3/502738 |
| | | | 422/63 |
| 2005/0151689 A1 | 7/2005 | Vesterinen | |
| 2008/0294029 A1 | 11/2008 | Piveteau | |
| 2008/0297169 A1 | 12/2008 | Matthias et al. | |
| 2010/0222652 A1 | 2/2010 | Cho | |
| 2014/0161668 A1 | 6/2014 | Colella et al. | |
| 2015/0245791 A1 | 9/2015 | Buse | |
| 2015/0253343 A1 | 9/2015 | Pearce | |
| 2015/0305681 A1 | 10/2015 | Nadkarni | |
| 2015/0346131 A1 | 12/2015 | Mohseni | |
| 2015/0375891 A1 | 12/2015 | Nameth | |
| 2016/0091455 A1 | 3/2016 | Taylor | |
| 2016/0091508 A1 | 3/2016 | Zhao et al. | |
| 2016/0091509 A1 | 3/2016 | Di Tullio | |
| 2016/0091510 A1 | 3/2016 | Di Tullio | |
| 2016/0091511 A1 | 3/2016 | Di Tullio | |
| 2016/0363600 A1 | 12/2016 | Sniadecki et al. | |
| 2017/0184545 A1 * | 6/2017 | Azpiroz | G01N 27/44791 |
| 2017/0231574 A1 | 8/2017 | Crawford | |
| 2018/0015475 A1 * | 1/2018 | Arlett | B01L 3/527 |
| 2018/0017517 A1 | 1/2018 | Werner et al. | |
| 2018/0087548 A1 | 3/2018 | Duffer | |
| 2018/0113111 A1 | 4/2018 | Yaralioglu | |

FOREIGN PATENT DOCUMENTS

| | | |
|---|---|---|
| CN | 108780056 B | 3/2022 |
| JP | 2004020367 | 1/2004 |
| WO | 2018208610 | 11/2018 |

OTHER PUBLICATIONS

Suster et al., An RF/microwave microfluidic sensor based on a 3D capacitive structure with a floating electrode for miniaturized dielectric spectroscopy, Sensors, 2014 IEEE, Valencia, Spain, 2014, pp. 1784-1787 (Year: 2014).*

International Search Report filed in PCT/US19/61368 dated Feb. 21, 2020.

EP office action filed in Appl. No. 19 886 562.8 dated Apr. 6, 2023.

Supplementary European Search Report in App. No. EP 19886562, dated Jul. 5, 2022.

* cited by examiner

PORTABLE DIELECTRIC SPECTROSCOPY DEVICE

BACKGROUND

Dielectric spectroscopy (DS) has been described as a useful analytical tool in the biomedical field as a label-free, non-destructive and real-time method to study the interaction of RF/microwave fields with biological/biochemical samples while requiring minimal sample preparation. Molecular characteristics of biomaterials such as human blood, spinal fluid, breast tissue and skin have been studied using DS for applications in disease detection and clinical diagnosis. Typical DS systems, however, tend to be large and expensive, making them cost-prohibitive in certain circumstances.

U.S. Pat. No. 9,995,701 B2 describes a DS system to measure dielectric permittivity. The DS system includes a sensing apparatus and a sensor interface system. The sensor interface system drives sensor circuitry, which is connected with electrodes positioned in a fluid channel of the sensing apparatus, with an RF input signal. The sensor circuitry is configured to have a dielectric permittivity that depends on fluid that is within the fluid channel. Another electrode also positioned in the fluid channel provides a corresponding RF output signal to a receiver in the sensor interface system that is connected with a computing system. The computing system is programmed with processing algorithms for computing permittivity in response to the RF output data provided by the receiver.

Improvements can be made in the aforementioned DS system to make the system more portable, intuitive and user friendly.

SUMMARY

In view of the foregoing, a portable DS device includes a device housing, device-side electrical contacts, a computing system and a removable sensor receiver assembly. The device housing includes a removable sensor receiver compartment. The device-side electrical contacts are positioned in or adjacent to the removable sensor receiver compartment. The computing system is in the device housing, is in communication with the device-side electrical contacts and includes an impedance analyzer. The removable sensor receiver assembly includes a removable sensor receiver housing configured to be selectively received in and removable from the removable sensor receiver compartment. The removable sensor receiver housing includes a fluid sensing apparatus receiving section configured to receive an associated fluid sensing apparatus in which a fluid to be tested is loaded. The removable sensor receiver assembly is also configured to provide for an electrical connection between the associated fluid sensing apparatus and the device-side electrical contact when the removable sensor receiver housing is received in the removable sensor receiver compartment.

Also, a removable sensor receiver assembly for use with a portable DS device includes a removable sensor receiver housing and at least two electrical contacts provided on the removable sensor receiver housing. The removable sensor receiver housing includes a fluid sensing apparatus receiving section configured to receive a fluid sensing apparatus in which a fluid to be tested is loaded. The electrical contacts are provided on the removable sensor receiver housing to provide for an electrical connection between the fluid sensing apparatus and an impedance analyzer on the portable DS device when the removable sensor receiver housing is received in a removable sensor receiver compartment of the portable DS device.

DETAILED DESCRIPTION

Figure 1:
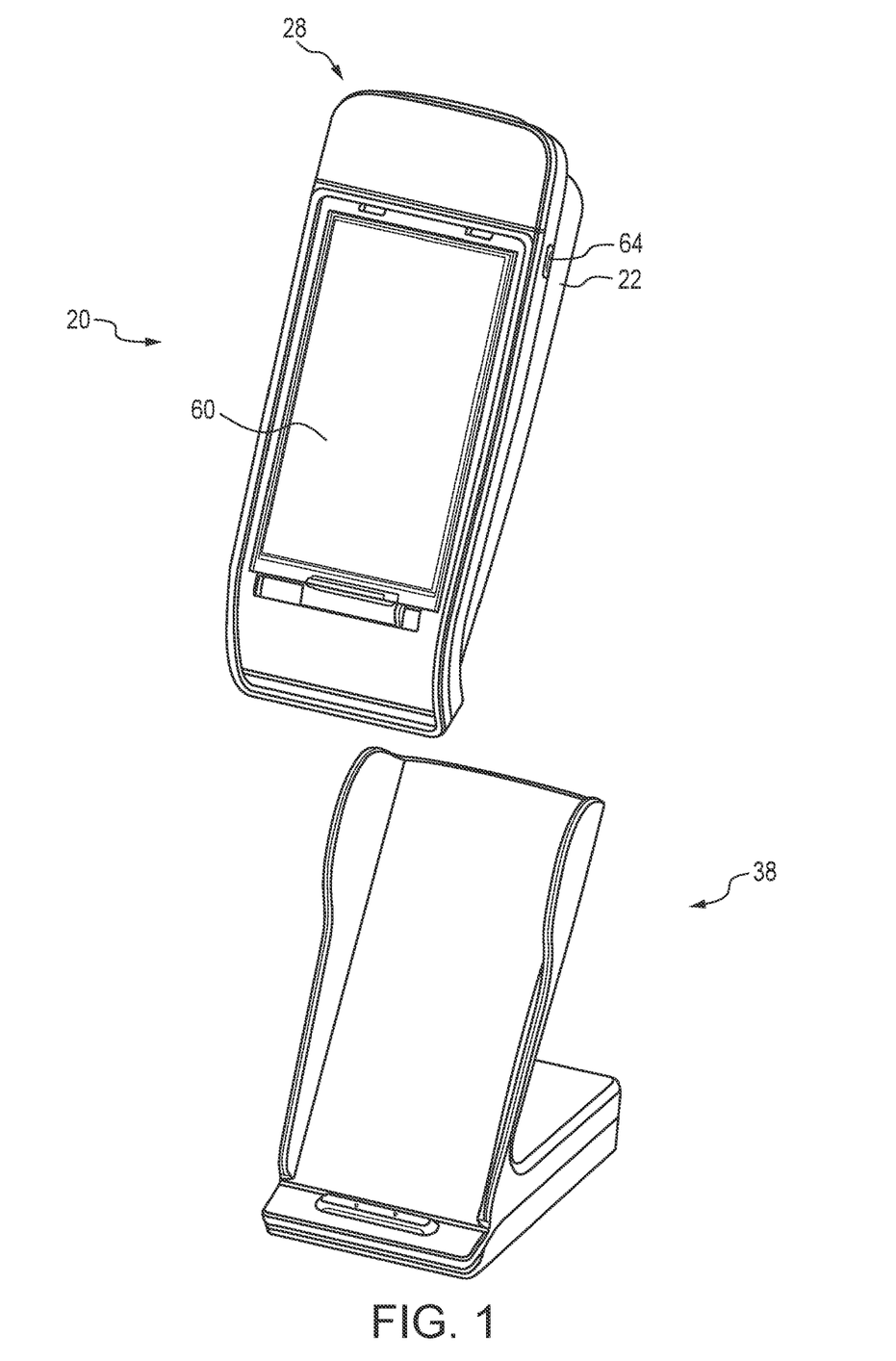
FIG. 1 is a front perspective view of a portable dielectric spectroscopy (DS) device with a respective docking station.

FIG. 1 schematically depicts a portable dielectric spectroscopy (DS) device 20 that is useful for the quantitative measurement of complex dielectric permittivity of a material versus frequency. The portable DS device 20 can be used for chemical analysis of many fluids including, but not limited to, blood to help determine whether certain drugs that may affect the coagulation rate of the blood are found in a blood sample. As such, the portable DS device 20 may be used as a portable coagulometer. The portable DS device 20, however, can be used for other quantitative measurements as well.

With continued reference to FIG. 1, the portable DS device 20 includes a device housing 22 that can house internal components of the portable DS device 20. The device housing 22 can be made of any suitable materials to house electrical components, which will be described in more detail below. The device housing 22 can be similar in size to a mobile phone, although slightly larger, so as to be easily grasped and manipulated by a human hand thus making the portable DS device 20 a hand held device.

Figure 2:
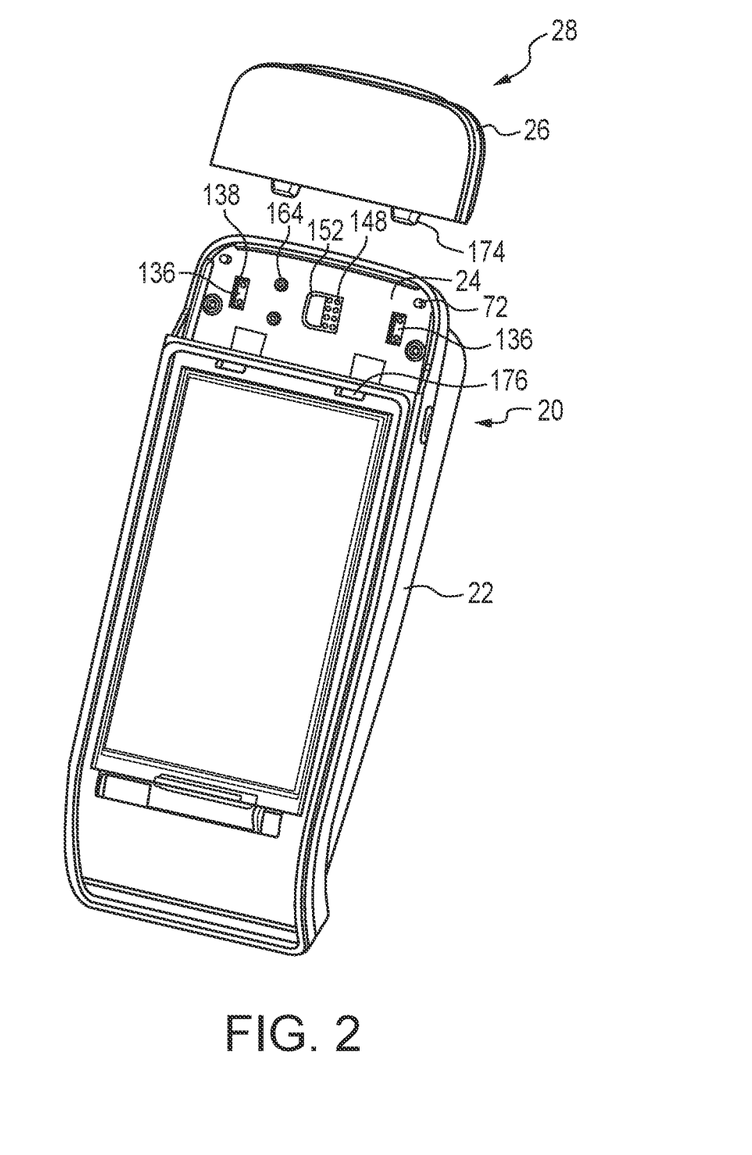
FIG. 2 is a perspective view of the portable DS device with a removable sensor receiver (RSR) assembly not yet loaded into the portable DS device.

With reference to FIG. 2, the device housing 22 includes a removable sensor receiver (RSR) compartment 24 that is configured to receive an RSR housing 26 of an RSR assembly 28, which will be described in more detail below. The RSR assembly 28, and thus the RSR housing 26, is/are insertable into and removable from the RSR compartment 24, which can allow for easier cleaning of the portable DS device 20 as well as allowing for other advantages that will be described in more detail below.

Figure 3:
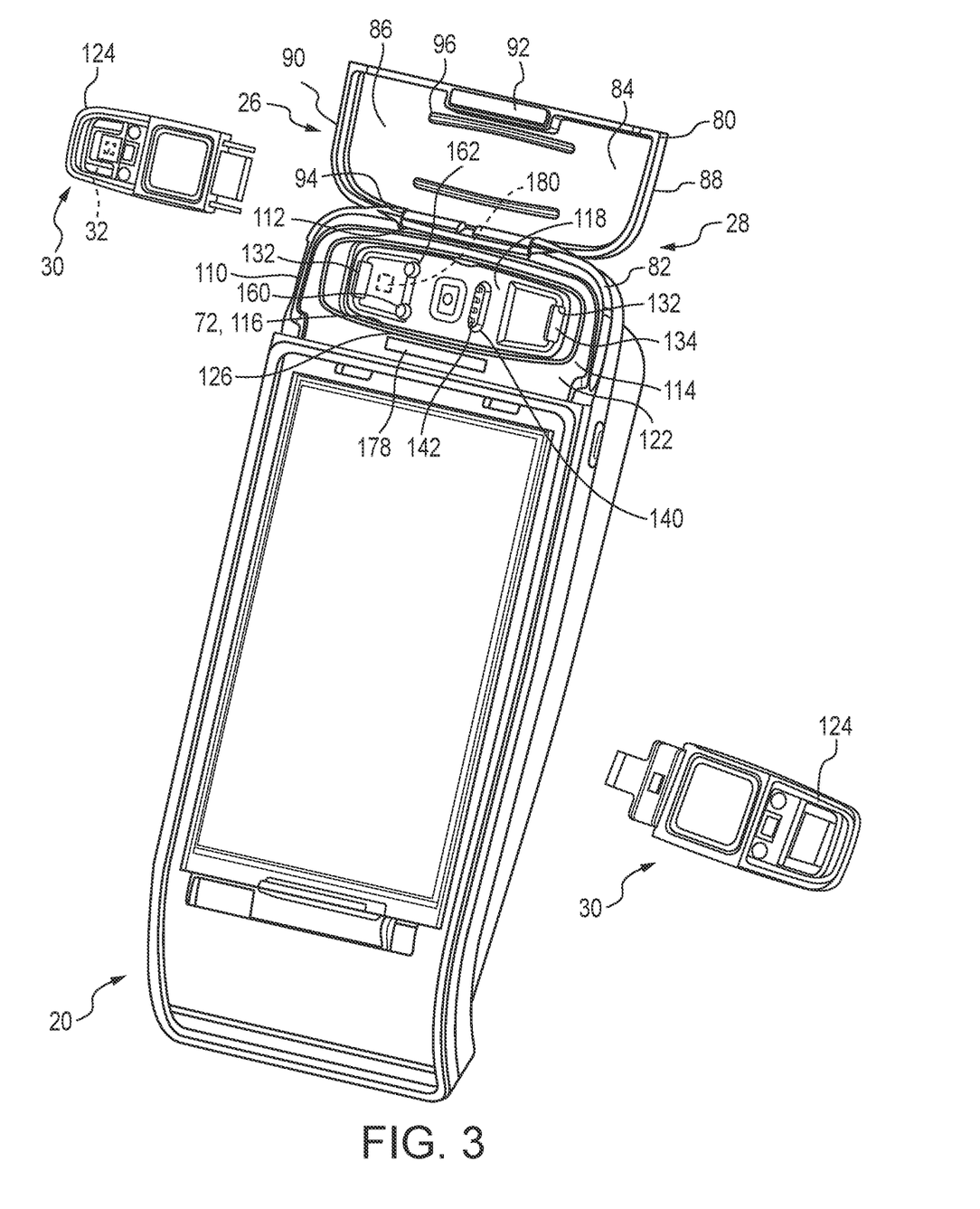
FIG. 3 is a perspective view of the portable DS device with the RSR assembly loaded into the portable DS device and two fluid sensing apparatuses not loaded into the RSR assembly.

With reference to FIG. 3, the RSR housing 26 receives a fluid sensing apparatus 30 in which a fluid sample 32 (schematically depicted in FIG. 3) to be tested is loaded. The fluid sensing apparatus 30 includes circuitry residing in a compartment in which the fluid sample 32 to be tested resides. The circuitry is configured to have a dielectric permittivity that depends on the fluid sample 32 being tested. The sensor circuitry is more particularly described in U.S.

Pat. No. 9,995,701 B2 as well as in U.S. provisional patent application No. 62/832,933. When the fluid sample 32 to be tested is blood, for example, allowing the RSR assembly 28 to be removable from the device housing 22 allows for easier cleaning of the portable DS device 20; however, providing for an electrical connection between the portable DS device 20 and the fluid sample 32 in the fluid sensing apparatus 30 must be taken into consideration.

Figure 4:
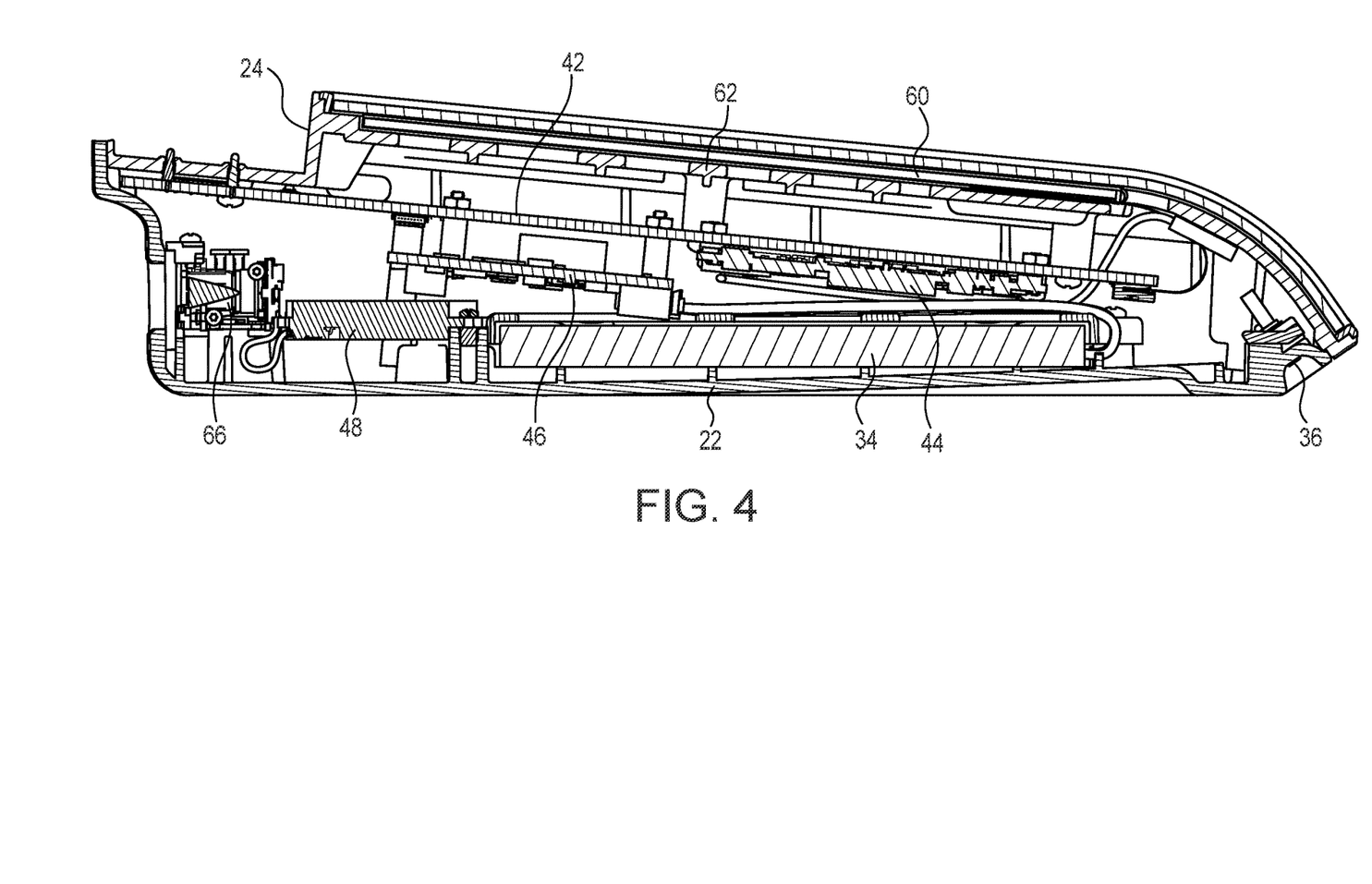
FIG. 4 is a schematic cross-sectional depiction of the portable DS device without the RSR assembly loaded into the portable DS device.

With reference to FIG. 4, a rechargeable battery 34 is disposed in the device housing 22. The rechargeable battery 34 can be in electrical contact with charging contacts 36. The portable DS device 20 can be placed on a docking station 38 (FIG. 1), which can connect with an electrical outlet in a conventional manner, to charge the portable DS device 20 in a manner similar to other small portable electronics.

Figure 5:
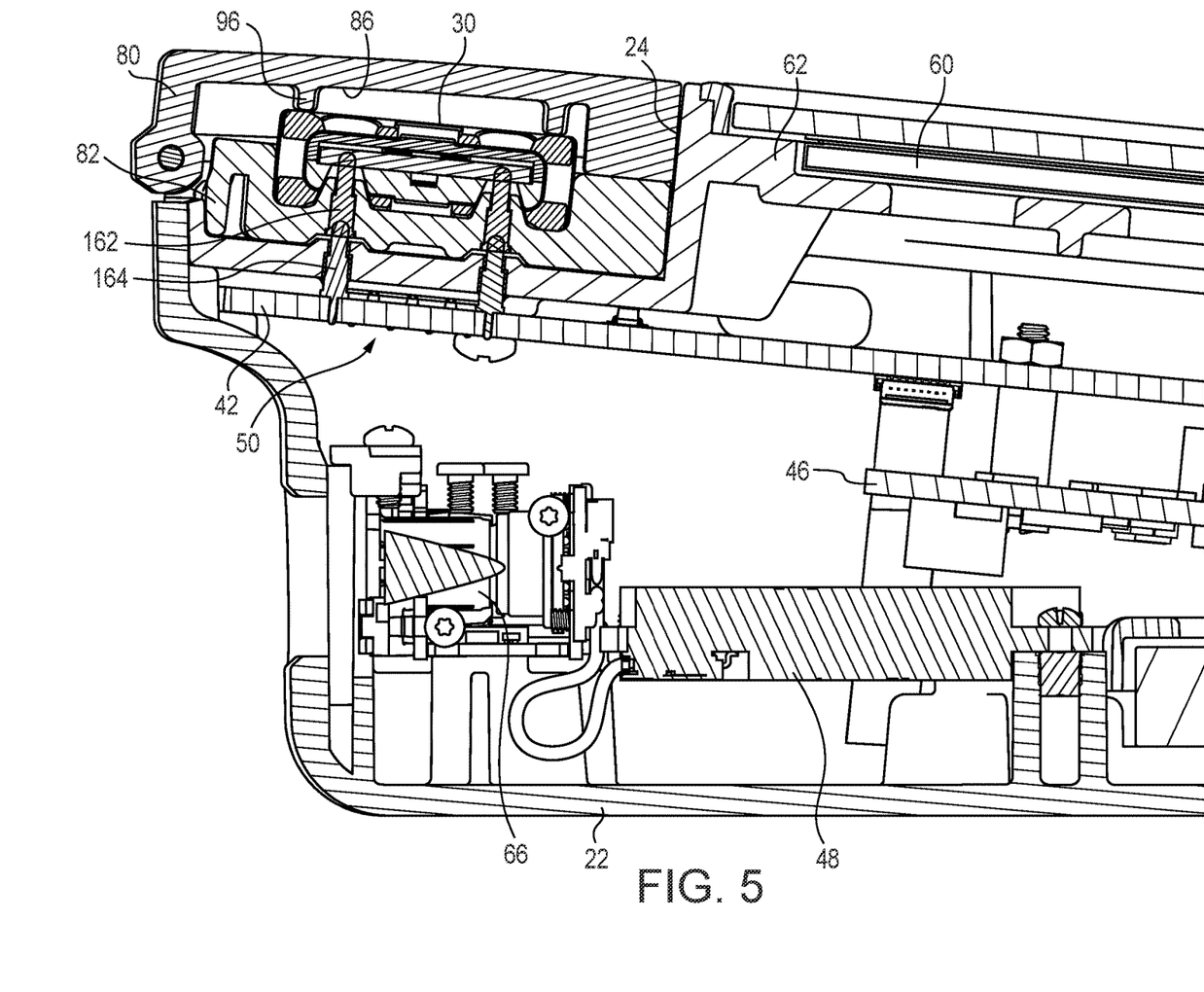
FIG. 5 is a schematic cross-sectional depiction of a portion of the portable DS device with the RSR assembly loaded into the portable DS device.

With continued reference to FIG. 4, the portable DS device 20 further includes a computing system, which can include programmable integrated circuits, system on modules (SOM) boards, field-programmable gate arrays (FPGA), and similar devices to operate the electrical components described below. FIG. 4 depicts one example in which the computing system includes a main circuit board 42 with FPGA, a SOM board 44, a power supply board 46, a scanner/decoder board 48, and miniature impedance analyzer components 50 (FIG. 5) being located on the main circuit board 42. Each component of the computing system is electrically connected with the battery 34 so as to receive power from the battery 34. FIGS. 4 and 5 depict one example of a computing system including a plurality of boards, however, any computing system capable of performing the functions described below could also be employed.

In the illustrated embodiment, the miniature impedance analyzer components 50 are located proximal to the RSR compartment 24 so as to inhibit the likelihood of interference and noise with regard to electrical communication between the miniature impedance analyzer components 50 and the fluid sample 32 being tested within the RSR compartment 24. In one particular embodiment, the miniature impedance analyzer components 50 are positioned within one centimeter of the fluid being tested within the RSR compartment 24 when a test is being run. As explained in U.S. Pat. No. 9,995,701 B2, when performing impedance analyzation on a fluid, measured signals are amplified in the miniature impedance analyzer components 50, and thus the minimization of interference and other noise signals is very useful. The miniature impedance analyzer components 50 can be similar to those described in U.S. Pat. No. 9,995,701 B2 for measuring the impedance and dielectric permittivity of the fluid sample 32 in the fluid sensing apparatus 30.

The portable DS device 20 further includes a display screen 60 on the device housing 22. The display screen 60 is useful to present information to a user of the portable DS device 20. The display screen 60 can be a thin-film-transistor (TFT) display such as those used with mobile phones. The display screen 60 is in electrical communication with the aforementioned computing system and receives power from the battery 34. A structural support 62 is disposed in the device housing 22 to provide structural support behind the display screen 60.

With reference back to FIG. 1, the portable DS device 20 can further include a USB-C connector 64 on the device housing 22. The USB-C connector 64 can allow for the electrical connection of an external device or computer to communicate with the aforementioned computing system to debug the portable DS device 20 as well as to program the computing system. Other types of connectors that allow for the connection of an external computing device can also be employed.

With reference to FIG. 4, the portable DS device 20 can further include a scanner camera 66 positioned within the device housing 22 and including a lens that is directed outwardly from the device housing 22. The scanner camera 66 is in electrical communication with the scanner/decoder board 48, which is part of the aforementioned computing system, to allow for the scanning of bar codes and other machine-readable indicia. This can be useful to associate the fluid sample 32 to be tested by the portable DS device 20 with a particular sample and/or patient.

The portable DS device 20 can further include buttons or other similar user interface devices to control the operation of the portable DS device 20 in general, for example, a button 68 (FIG. 6) which can control the on/off function of the portable DS device 20 as well as to control the scanner camera 66 and other components on the portable DS device 20 is provided.

The RSR assembly 28 includes the RSR housing 26, which is configured to be received inside the RSR compartment 24 as shown in FIGS. 1, 3 and 5. The RSR housing 26 includes a fluid sensing apparatus receiving section 72 configured to receive the fluid sensing apparatus 30. The RSR assembly 28 is also configured to provide for an electrical connection between the fluid sensing apparatus 30 and the computing system and the miniature impedance analyzer components 50 via device-side electrical contacts (described in more detail below) when the RSR housing 26 is received in the RSR compartment 24.

The RSR housing 26 includes a lid 80 movably connected with a back panel 82. The lid 80 includes a lid ceiling 84 defining a ceiling inner surface 86 and a ceiling outer surface 88. When the lid 80 is closed with respect to the back panel 82, such as that shown in FIG. 2, the ceiling inner surface 86 faces toward the fluid sensing apparatus receiving section 72 and the fluid sensing apparatus 30 if it is loaded into the RSR assembly 28. A peripheral rim 90 extends away from the lid ceiling 84 and more particularly the ceiling inner surface 86. A magnet 92 is provided near the peripheral rim 90 and cooperates with the back panel 82 to retain the lid 80 in the closed position when the lid 80 is closed over the back panel 82. The lid 80 further includes axle hubs 94 that receive an axle (not visible) connecting the lid 80 with the back panel 82 in a pivotal manner. The lid 80 is shown pivotally connected with the back panel 82; however, the lid 80 could connect with the back panel 82 in other movable manners, such as being slidable with respect to the back panel 82. The lid 80 includes sensor contact flanges 96 that also depend away from the lid ceiling 84 and more particularly the ceiling inner surface 86 in the same direction as the peripheral rim 90. Each sensor contact flange 96 extends downwardly from the ceiling inner surface 86 when the lid 80 is in the closed position (FIG. 5). The sensor contact flange 96 is configured to contact the fluid sensing apparatus 30 and urge the fluid sensing apparatus 30 toward electrical contacts (described in more detail below) when the lid 80 is in the closed position.

The back panel 82 includes a peripheral ridge 110 having an axle hub receiving recess 112 that receives the axle hubs 94 on the lid 80. The peripheral ridge 110 extends away from a floor 114 of the back panel 82. The floor 114 includes a recess 116 to separate a recessed floor surface 118 from an elevated floor surface 122. In the illustrated embodiment, the recess 116 coincides with the fluid sensing apparatus receiving section 72. The fluid sensing apparatus 30 and the recess 116 are each configured so that the fluid sensing apparatus 30 is received within the recess 116 in only one orientation. The fluid sensing apparatus 30 includes a cap 124 that is receivable on opposite ends of the fluid sensing apparatus 30. In FIG. 3, the fluid sensing apparatus 30 is shown on the left of the portable DS device 20 in the configuration in which the fluid sample 32 has been loaded into the fluid sensing apparatus 30 and the fluid sample 32 is ready to be tested. Also in FIG. 3, the fluid sensing apparatus 30 is shown on the right of the portable DS device 20 in the configuration in which the fluid sample 32 has yet to be loaded into the fluid sensing apparatus 30 and the cap 124 is at the opposite end. The fluid sensing apparatus 30 is receivable within the recess 116 with the cap 124 at either end; however, the appropriate side of the fluid sensing apparatus 30 needs to be facing the recessed floor surface 118 and the cap 124 needs to be appropriately attached for the fluid sensing apparatus 30 to be properly received in the recess 116. Small protrusions 126 can extend into the recess 116 to facilitate alignment of the fluid sensing apparatus 30 and to preclude the fluid sensing apparatus 30 from being received in the recess 116 in an improper orientation.

The back panel 82 includes at least two position sensor openings 132. Each position sensor opening 132 receives a respective position sensor window 134, which is translucent or transparent. Each position sensor opening 132 is configured for alignment with a respective position sensor 136 (FIG. 2) on the portable DS device 20. Each position sensor 136 can be mounted to the main circuit board 42 (see FIG. 4). At least two position sensor apertures 138, which are each aligned with a respective position sensor 136, are provided in the device housing 22 in the RSR compartment 24. When the RSR housing 26 is received in the RSR compartment 24, the at least two position sensor apertures 138 are each aligned with a respective position sensor window 134 on the removable sensor receiver housing 26. The position sensor openings 132 are provided within the recess 116 and extend through the recessed floor surface 118. The position sensors 136 can be optical position sensors and be configured to detect a relative location of the lid 80 with respect to the back panel 82. For example, the position sensors 136 can provide a signal to indicate that the lid 80 is either opened or closed. Additionally, each of the position sensors 136 is provided in an appropriate location to allow for detection of a relative location of the cap 124 on the fluid sensing apparatus 30 to be determined. As indicated above, for the fluid sensing apparatus 30 shown on the left of the portable DS device 20, the cap 124 is shown over a first end of the fluid sensing apparatus 30. The cap 124 can also connect with the opposite end of the fluid sensing apparatus 30, which is shown for the fluid sensing apparatus 30 shown on the right of the portable DS device 20 in FIG. 3. When the cap 124 is on the first end of fluid sensing apparatus 30, the position sensor 136 on the left in FIG. 2 can detect the presence of the cap 124. When the cap 124 is on the second end of fluid sensing apparatus 30 (such as that shown for the fluid sensing apparatus on the right of the portable DS device in FIG. 3), the position sensor 136 on the right in FIG. 2 can detect the presence of the cap 124.

A control electrical contact opening 140 is provided through the floor 114 of the back panel 82 within the recess 116. A plurality of RSR-side control electrical contacts 142, which can be in the form of pogo pins, extend through the control electrical contact opening 140. The RSR-side control electrical contacts 142 are mounted to a small circuit board 144 (FIG. 6) mounted to a rear surface 146 of the back panel 82. The RSR-side control electrical contacts 142 provide an electrical connection between electrical components on the fluid sensing apparatus 30 that can for example control a heater (not shown in FIG. 3) on the fluid sensing apparatus 30 to maintain the fluid sample 32 within a desired temperature range. The RSR-side control electrical contacts 142 can also provide signals to allow for an identification of the fluid sensing apparatus 30. The RSR-side control electrical contacts 142 connect with device-side control electrical contacts 148 (FIG. 2), which can also be in the form of pogo pins, provided on the portable DS device 20. The device-side control electrical contacts 148 can be provided in the RSR compartment 24 extending through an opening 152 provided therein. The device-side control electrical contacts 148 can also be mounted to the main circuit board 42 (see FIG. 7).

With reference back to FIG. 3, at least two RSR-side impedance analyzer contacts 160 each extend through a respective RSR-side impedance analyzer contact opening 162 provided in the back panel 82. Each of the RSR-side impedance analyzer contacts 160 are provided within the recess 116 and extend upwardly from the recessed floor surface 118. Each of the RSR-side impedance analyzer contacts 160 can be in the form of a pogo pin. With reference now also to FIG. 2, each of the at least two RSR-side impedance analyzer contacts 160 electrically contacts a respective device-side impedance analyzer contact 164 when the RSR housing 26 is received in the RSR compartment 24. With reference to FIG. 5, the device-side impedance analyzer contacts 164 can make up a portion of the miniature impedance analyzer components 50, which can be provided on the main circuit board 42.

Figure 6:
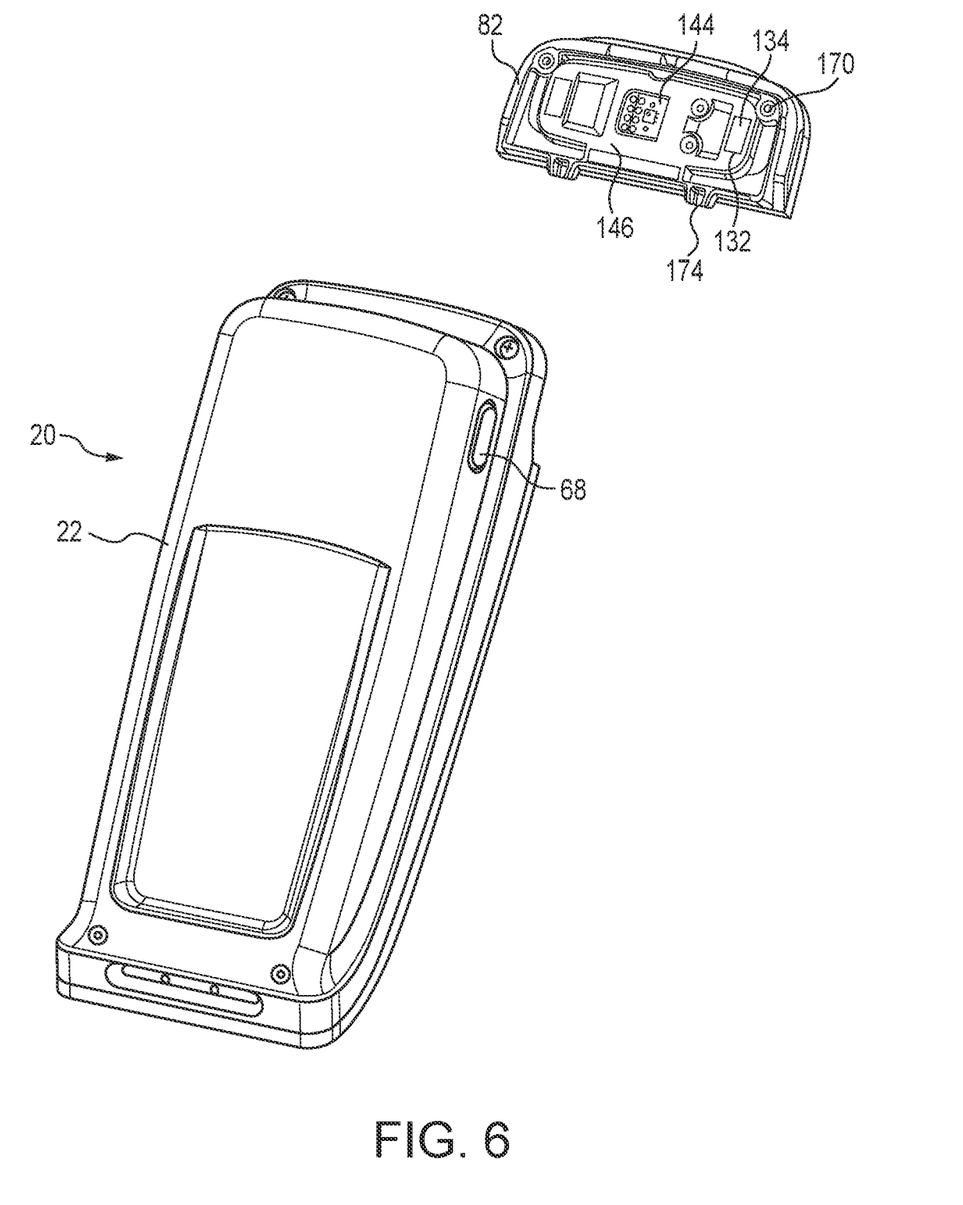
FIG. 6 is a rear perspective view of the portable DS device with the RSR assembly not yet loaded into the portable DS device.
Figure 7:
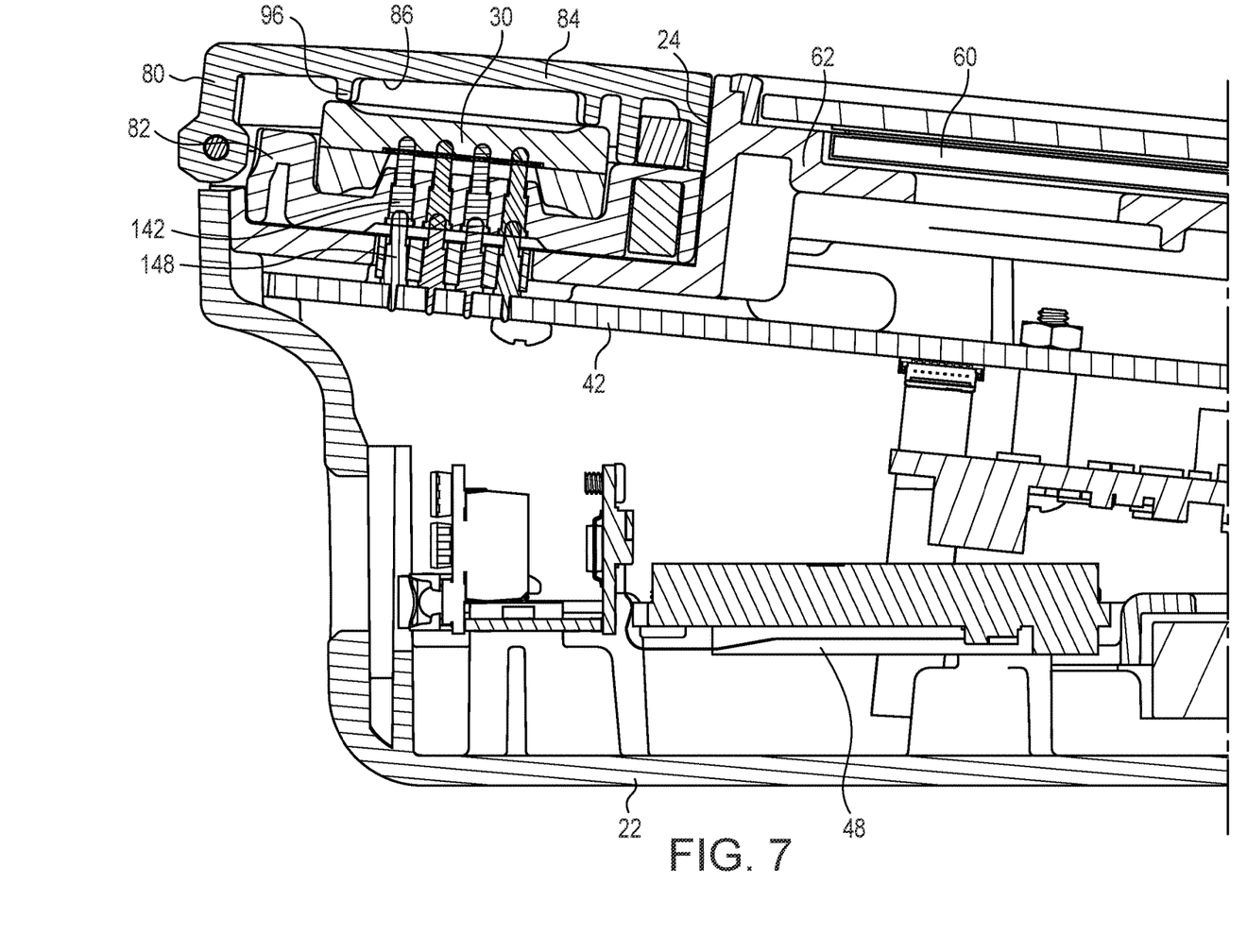
FIG. 7 is another schematic cross-sectional depiction of a portion of the portable DS device with the RSR assembly loaded into the portable DS device.

With reference to FIG. 6, the back panel 82 of the RSR housing 26 also includes stand off openings 170. With reference back to FIG. 2, each stand off opening 170 is configured to receive a respective stand off 172 provided in the RSR compartment 24. The stand off openings 170 cooperate with the stand offs 172 to properly align the RSR assembly 28 within the RSR compartment 24. Additionally, locator tabs 174 extend downwardly from the floor 114 of the back panel 82. Each locator tab 174 is received in a respective locator tab opening 176 provided in the RSR compartment 24. The locator tabs 174 on the RSR housing 26 cooperate with the locator tab openings 176 provided on the portable DS device 20 properly locate the RSR assembly 28 within the RSR compartment 24. With reference back to FIG. 3, a Hall-effect sensor 178 cooperates with the magnet 92 to indicate a closed position when the lid 80 is closed against the back panel 82.

The RSR assembly 28 can further include a heater 180, which is depicted in phantom in FIG. 3. The fluid sensing apparatus 30 depicted in FIG. 3 includes a heater (not visible) that is controlled via the device-side control electrical contacts 148 and the RSR-side control electrical contacts 142. If the fluid sensing apparatus 30 did not include the heater, however, or in addition to this heater, the heater 180 can connect with the battery 34 via the device-side control electrical contacts 148 when the RSR housing 26 is received in the RSR compartment 24. The heater 180 can positioned within the recess 116, which can allow the heater to maintain the fluid sample 32 to be tested in the fluid sensing apparatus 30 within a desired temperature range. A thermistor (not shown) or similar temperature sensor can be provided in the RSR assembly 28 and be in communication with the computing system via the device-side control electrical contacts 148 when the RSR housing 26 is received in the RSR compartment 24. The thermistor or similar temperature sensor can control the operation of the heater 180 so as to maintain the temperature of the fluid to be tested within the desired temperature range.

In operation, one removes the portable DS device 20 from the docking station 38. If the portable DS device 20 needs charging, then a message is displayed on the display screen 60 that the portable DS device needs charging and a test cannot be run. If the portable DS device 20 does not need charging, then user removes the fluid sensing apparatus 30 from sterile packaging. When in the sterile packaging, the cap 124 is connected with the end of the fluid sensing apparatus 30 shown in FIG. 3 for the fluid sensing apparatus 30 on the right of the portable DS device 20. The user can then press a button, similar to or the same as the on/off button 68 depicted in FIG. 6 or a "button" provided on the display screen 60, to operate the scanner camera 66 to scan a data matrix label (not shown) on the fluid sensing apparatus 30. The user then opens the lid 80 of the RSR housing 26 and places the fluid sensing apparatus 30 with the cap 124 connected in the manner shown to the right of the portable DS device 20 in FIG. 3 in the recess 116.

The lid 80 is then closed, which can be confirmed by the position sensors 136. The computing system on the portable DS device 20 is configured to determine the temperature of the portable DS device 20 via a thermistor provided on the portable DS device 20, which is in electrical communication with the thermistor via the device-side control electrical contacts 148 and the RSR-side control electrical contacts 142. If the thermistor measures a temperature outside of a predefined temperature range, then the computing system can operate the heater on the fluid sensing apparatus 30 (or operate the optional heater 180) to heat the portable DS device 20. During this pre-heating stage, the display screen 60 can indicate to the user that the fluid sensing apparatus 30 is being pre-heated. The location of the cap 124 on the fluid sensing apparatus 30 can be confirmed by the position sensors 136.

During the pre-heating stage, the user can then press a button, similar to or the same as the on/off button 68 depicted in FIG. 6 or a "button" provided on the display screen 60, to operate the scanner camera 66 to scan a patient identification, which is associated with the patient from which fluid will be drawn. Optionally, the user can enter the patient identification information manually using the display screen 60. Other information, such as when the last time the patient took medication, can also be entered into the computing system via the display screen 60.

While the portable DS device 20 is in the pre-heating stage, if the pre-heating stage is necessary, the patient can be prepped for taking the fluid sample. For example, when the fluid sample is to be blood, the patient's finger can be cleaned and pricked. When the thermistor on the fluid sensing apparatus 30 measures a predetermined temperature, e.g. 37 degrees C., the lid 80 can be opened and the fluid sensing apparatus 30 can be removed from the RSR housing 26. Because of the position sensors 136, the relative location of the lid 80 with respect to the back panel 82 is known. The computing system can then begin a timer to provide the user a predetermined amount of time, e.g., between about 30 and 45 seconds, to obtain the fluid sample within the fluid sensing apparatus 30, to place the cap 124 on the fluid sensing apparatus 30 (i.e., the position shown on the left of the portable DS device in FIG. 3) to cover the fluid sample 32, to place the fluid sensing apparatus 30 back into the recess 116 of the RSR assembly 28 and to close the lid 80.

If the predetermined amount of time expires before the fluid sensing apparatus 30 is placed back into the recess 116 of the RSR assembly 28 and the lid 80 is closed, then the display screen 60 can provide an indication to the user that a new fluid sample needs to be obtained with a new the fluid sensing apparatus 30. If the fluid sensing apparatus 30 is placed back into the recess 116 of the RSR assembly 28 and the lid 80 is closed within the predetermined amount of time, then a verification procedure can take place.

The verification procedure can include the computing system determining whether impedance values being measured for the fluid to be tested falls within a predetermined range of values, so as to provide an indication that the appropriate fluid is being tested. The verification procedure also includes the computing system determining whether the cap 124 is on over the fluid sample 32. The position sensor 136 can detect the presence of the cap 124. The verification procedure also includes the computing system determining that the heater and the thermistor on the fluid sensing apparatus 30 return known values and change (i.e., increase at a rate that can be verified). The verification procedure also includes the computing system determining that the RSR housing 26 lid 80 is closed, which can be determined by the magnet 92 and the Hall-effect sensor 178. The verification procedure can also include the computing system determining whether the thermistor (not shown) or similar temperature sensor provided in the RSR assembly 28 (i.e., not in the fluid sensing apparatus 30) returns a value within a predetermined range. If the fluid sensing apparatus 30 is properly verified, then the analysis testing on the fluid sample 32 is performed.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A portable dielectric spectroscopy (DS) device comprising:
   a device housing including a removable sensor receiver compartment;
   at least one device-side electrical contact positioned in or adjacent to the removable sensor receiver compartment;
   a computing system in the device housing, in communication with the at least one device-side electrical contact and including an impedance analyzer; and
   a removable sensor receiver assembly including a removable sensor receiver housing configured to be received in the removable sensor receiver compartment and including a sensing apparatus receiving section configured to receive an associated sensing apparatus in which a fluid sample to be tested is loaded and to provide for an electrical connection between the associated sensing apparatus and the at least one device-side electrical contact when the removable sensor receiver housing is received in the removable sensor receiver compartment; and
   at least two position sensors in communication with the computing system and configured to detect a relative location of an associated cap for the associated sensing apparatus.

2. The portable DS device of claim 1, wherein the at least two position sensors include a first position sensor configured to detect whether the associated cap is connected with the associated sensing apparatus at a first end of the associated sensing apparatus and a second position sensor spaced from the first position sensor and configured to detect whether the associated cap is connected with the associated sensing apparatus at a second end of the associated sensing apparatus.

3. The portable DS device of claim 1, wherein the removable sensor receiver housing includes a lid movably connected with a back panel, wherein the back panel includes at least two position sensor openings each aligned with a respective position sensor of the at least two position sensors.

4. The portable DS device of claim 3, wherein each of the at least two position sensors is further configured to detect a relative location of the lid with respect to the back panel.

5. The portable DS device of claim 1, wherein the at least two position sensors are mounted in the device housing and at least two position sensor apertures, which are each aligned with a respective position sensor, are provided in the device housing in the removable sensor receiver compartment, when the removable sensor receiver housing is received in the removable sensor receiver compartment the at least two position sensor apertures are each aligned with a respective position sensor window on the removable sensor receiver housing.

6. The portable DS device of claim 1, wherein the at least one device-side electrical contact includes at least one device-side control contact in communication with the computing system, which is configured to control operation of a heater.

7. The portable DS device of claim 6, wherein the at least one device-side control contact includes a plurality of pogo pins provided in the removable sensor receiver compartment, the plurality of pogo pins being configured to contact RSR-side control electrical contacts provided on the removable sensor receiver housing when the removable sensor receiver housing is received in the removable sensor receiver compartment.

8. The portable DS device of claim 7, wherein the at least one device-side control contact further includes at least two device-side impedance analyzer contacts in communication with the impedance analyzer.

9. The portable DS device of claim 8, wherein the removable sensor receiver assembly includes at least two RSR-side impedance analyzer contacts, wherein each of the at least two device-side impedance analyzer contacts electrically contacts a respective RSR-side impedance analyzer contact of the at least two RSR-side impedance analyzer contacts when the removable sensor receiver housing is received in the removable sensor receiver compartment.

10. The portable DS device of claim 1, further comprising at least one standoff extending away from the device housing in the removable sensor receiver compartment, wherein the removable sensor receiver housing includes at least one standoff opening, each standoff opening of the at least one standoff opening receives a respective standoff of the at least one standoff when the removable sensor receiver housing is received in the removable sensor receiver compartment.

11. The portable DS device of claim 1, further comprising at least one locator tab opening open to the removable sensor receiver compartment, wherein the removable sensor receiver housing includes at least one locator tab, each locator tab opening of the at least one locator tab opening receives a respective locator tab of the at least one locator tab when the removable sensor receiver housing is received in the removable sensor receiver compartment.

12. A removable sensor receiver assembly for use with an associated portable dielectric spectroscopy (DS) device, the removable sensor receiver assembly comprising:

a removable sensor receiver housing including a sensing apparatus receiving section configured to receive an associated sensing apparatus in which a fluid sample to be tested is loaded;

at least two RSR-side electrical contacts provided on the removable sensor receiver housing to provide for an electrical connection between the associated sensing apparatus and an associated impedance analyzer on the associated portable DS device when the removable sensor receiver housing is received in a removable sensor receiver compartment of the associated portable DS device; and a lid movably connected with a back panel, wherein the back panel includes at least two position sensor openings each configured for alignment with a respective position sensor on the associated portable DS device configured to detect a relative location of the lid with respect to the back panel.

13. The removable sensor receiver assembly of claim 12, wherein the back panel defines a recess in an elevated floor surface, wherein the recess defines the sensing apparatus receiving section and a recessed floor surface within the recess includes at least two position sensor openings each configured for alignment with a respective position sensor on the associated portable DS device configured to detect a relative location of an associated cap for the associated sensing apparatus.

14. The removable sensor receiver assembly of claim 12, wherein the lid includes at least one sensor contact flange extending downwardly from a ceiling inner surface when the lid is in a closed position, the at least one sensor contact flange configured to contact the associated sensing apparatus and urge the associated sensing apparatus toward the at least two RSR electrical contacts when the lid is in the closed position.

15. The removable sensor receiver assembly of claim 12, wherein the at least two RSR-side electrical contacts includes electrical contacts to provide for an electrical connection between an associated heater on the associated sensing apparatus and an associated computer system on the associated portable DS device for controlling the associated heater when the removable sensor receiver housing is received in the removable sensor receiver compartment of the associated portable DS device.

16. The removable sensor receiver assembly of claim 15, wherein the electrical contacts that provide for an electrical connection between the associated heater on the associated sensing apparatus and the associated computer system on the associated portable DS device for controlling the associated heater are pogo pins mounted to a circuit board connected with the removable sensor receiver housing.

17. A portable dielectric spectroscopy (DS) system comprising:

a fluid sensing apparatus configured to receive a fluid sample to be tested; and a portable dielectric spectroscopy (DS) device including a device housing having a removable sensor receiver compartment, at least one device-side electrical contact positioned in or adjacent to the removable sensor receiver compartment, a computing system in the device housing in communication with the at least one device-side electrical contact and including an impedance analyzer, and at least two position sensors in communication with the computing system and configured to detect a relative location of an associated cap for the sensing apparatus; and a removable sensor receiver assembly including a removable sensor receiver housing configured to be received in the removable sensor receiver compartment, the removable sensor receiver assembly including a sensing apparatus receiving section configured to receive the fluid sensing apparatus and to provide for an electrical connection between the fluid sensing apparatus and the at least one device-side electrical contact when the removable sensor receiver housing is received in the removable sensor receiver compartment with the fluid sensing apparatus received in the sensing apparatus receiving section of the removable sensor receiver assembly.

18. The portable DS system of claim 17, wherein the fluid sensing apparatus and the removable sensor receiver compartment are each configured so that the fluid sensing apparatus is received within the removable sensor receiver compartment in only one orientation.

19. The portable DS system of claim 18, wherein the fluid sensing apparatus includes a cap that is receivable on opposite ends of the fluid sensing apparatus.

20. The portable DS system of claim 19, wherein the fluid sensing apparatus is receivable within the removable sensor receiver compartment with the cap at either end; and the removable sensor receiver assembly includes protrusions configured to align the fluid sensing apparatus in the fluid sensing apparatus receiving section with the cap attached to one of the opposite ends of the fluid sensing apparatus for the fluid sensing apparatus to be properly received in the removable sensor receiver compartment.

* * * * *